US012664653B2

(12) United States Patent
Alsheimer et al.

(10) Patent No.: US 12,664,653 B2
(45) Date of Patent: Jun. 23, 2026

(54) CAPTURE CONSTRUCT AND METHOD FOR DETECTING A PLURALITY OF ANALYTES

(71) Applicant: LEICA MICROSYSTEMS CMS GMBH, Wetzlar (DE)

(72) Inventors: Soeren Alsheimer, Wetzlar (DE); Arnold Giske, Wetzlar (DE)

(73) Assignee: LEICA MICROSYSTEMS CMS GMBH, Wetzlar (DE)

( * ) Notice: Subject to any disclaimer, the term of this patent is extended or adjusted under 35 U.S.C. 154(b) by 432 days.

(21) Appl. No.: 18/284,550

(22) PCT Filed: Mar. 31, 2022

(86) PCT No.: PCT/EP2022/058640
§ 371 (c)(1),
(2) Date: Sep. 28, 2023

(87) PCT Pub. No.: WO2022/207832
PCT Pub. Date: Oct. 6, 2022

(65) Prior Publication Data
US 2025/0084458 A1      Mar. 13, 2025

(30) Foreign Application Priority Data

Apr. 1, 2021    (WO) ................ PCT/EP2021/058785
May 4, 2021    (WO) ................ PCT/EP2021/061754
(Continued)

(51) Int. Cl.
*C12Q 1/68*          (2018.01)
*C12Q 1/6818*        (2018.01)
(Continued)

(52) U.S. Cl.
CPC .......... *G06T 7/0014* (2013.01); *C12Q 1/6818* (2013.01); *G01N 33/5094* (2013.01);
(Continued)

(58) Field of Classification Search
CPC ...................................................... C12Q 1/68
See application file for complete search history.

(56) References Cited

U.S. PATENT DOCUMENTS 10,024,796 B2 *    7/2018  Lin ...................... C12Q 1/6825
2014/0057805 A1    2/2014  Tinnefeld et al.

FOREIGN PATENT DOCUMENTS

EP          3 425 063 A1      1/2019
WO    WO 2015/188053 A1      12/2015
(Continued)

OTHER PUBLICATIONS

Youngeun Choi et al.: "A new reporter design based on DNA origami nanostructures for quantification of short oligonucleotides using microbeads", Scientific Reports, vol. 9, No. 1, Mar. 18, 2019 (Mar. 18, 2019), XP055728379, pp. 1-8.
(Continued)

*Primary Examiner* — Aaron A Priest
(74) *Attorney, Agent, or Firm* — LEYDIG, VOIT & MAYER, LTD.

(57) ABSTRACT

A capture construct for capturing a plurality of analytes of a biological sample includes a nanostructure backbone, at least a first orientation indicator and a second orientation indicator, and at least a first plurality of capture regions on the nanostructure backbone. Each capture region includes at least one affinity capture reagent configured to capture one of the plurality of analytes.

21 Claims, 14 Drawing Sheets

(30) Foreign Application Priority Data

| May 19, 2021 | (WO) | ................ PCT/EP2021/063310 |
|---|---|---|
| Jun. 18, 2021 | (WO) | ................ PCT/EP2021/066645 |
| Aug. 28, 2021 | (WO) | ................ PCT/EP2021/073819 |
| Sep. 3, 2021 | (WO) | ................ PCT/EP2021/074412 |

(51) Int. Cl.

| *G01N 33/50* | (2006.01) |
|---|---|
| *G01N 33/542* | (2006.01) |
| *G02B 21/36* | (2006.01) |
| *G06T 7/00* | (2017.01) |
| *H04N 13/207* | (2018.01) |

(52) U.S. Cl.

CPC ......... *G01N 33/542* (2013.01); *G02B 21/365* (2013.01); *H04N 13/207* (2018.05); *G01N 2458/10* (2013.01); *G06T 2200/04* (2013.01); *G06T 2207/10056* (2013.01); *G06T 2207/30024* (2013.01); *G06T 2207/30096* (2013.01); *G06T 2207/30204* (2013.01)

(56) References Cited

FOREIGN PATENT DOCUMENTS

| WO | WO 2019/109707 A1 | 6/2019 |
|---|---|---|
| WO | WO 2020/154595 A1 | 7/2020 |

OTHER PUBLICATIONS

Saccà, Barbara and Christof M. Niemeyer, "DNA-Origami: die Kunst, DNA zu falten," Angewandte Kurzaufsätze, Dec. 7, 2011, Wiley-VCH Verlag GmbH & Co. KGaA, Germany, pp. 60-69.

Rajendran, Arivazhagan et al., "Einzelmolekülanalysen mithilfe von DNA-Origami," Angewandte Kurzaufsätze, Nov. 25, 2011, Wiley-VCH Verlag GmbH & Co. KGaA, Germany, pp. 898-915.

Shaw, Alan et al., "Binding to nanopatterned antigens is dominated by the spatial tolerance of antibodies," nature nanotechnology, vol. 14, Feb. 2019, pp. 184-190, UK.

Saccà, Barbara et al., "Orthogonal Protein Decoration of DNA Origami," Angewandte Chemie, Oct. 28, 2010 , Wiley-VCH Verlag Gmbh & Co. KGaA, Germany, pp. 9568-9573.

Glasgow, Ben J., "Conventional fluorescence microscopy below the diffraction limit with simultaneous capture of two fluorophores in DNA origami," Proc. of SPIE vol. 9714, pp. 971411-1-971411-8, Jul. 7, 2016, US.

Uhlén, Mathias et al., "The human secretome," *Science Signaling*, Nov. 26, 2019: vol. 12, Issue 609, pp. 1-8, AAAS, US.

Wanxia Li Tsai et al., "High Throughput pSTAT Signaling Profiling by Fluorescent Cell Barcoding and Computational Analysis," J Immunol Methods. Feb. 2020; 477:112667, pp. 1-19, HHS Public Access, US.

Rodriguez, Erik A. et al., "The growing and glowing toolbox of fluorescent and photoactive proteins," Trends Biochem Sci. Feb. 2017; 42(2): 111-129, pp. 1-31, HHS Public Access, US.

Yan, Fanyong et al., "The fluorescence mechanism of carbon dots, and methods for tuning their emission color: a review," Jul. 29, 2019 in Microchimica Acta (2019) 186: 583, Springer-Verlag GmbH Austria, Austria, pp. 1-37.

Iravani, Siavash and Rajender S. Varma, "Green synthesis, biomedical and biotechnological applications of carbon and graphene quantum dots. A review," Environ Chem Lett. Mar. 10, 2020 : 1-25, Springer Nature Switzerland AG, Switzerland.

Kacenauskaite, Laura et al., "Rational Design of Bright Long Fluorescence Lifetime Dyad Fluorophores for Single Molecule Imaging and Detection," J. Am. Chem. Soc. 2021, 143, 1377-1385, Jan. 11, 2021, American Chemical Society, US.

* cited by examiner

CAPTURE CONSTRUCT AND METHOD FOR DETECTING A PLURALITY OF ANALYTES

CROSS REFERENCE TO RELATED APPLICATIONS

This application is a U.S. National Phase application under 35 U.S.C. § 371 of International Application No. PCT/EP2022/058640, filed on Mar. 31, 2022, and claims benefit to European Patent Application No. PCT/EP2021/074412, filed on Sep. 3, 2021, and European Patent Application No. PCT/EP2021/073819, filed on Aug. 28, 2021, and European Patent Application No. PCT/EP2021/066645, filed on Jun. 18, 2021, and European Patent Application No. PCT/EP2021/063310, filed on May 19, 2021, and European Patent Application No. PCT/EP2021/061754, filed on May 4, 2021, and European Patent Application No. PCT/EP2021/058785, filed on Apr. 1, 2021. The International Application was published in English on Oct. 6, 2022 as WO 2022/207832 A1 under PCT Article 21(2).

FIELD

Embodiments of the present invention relate to a capture construct for capturing a plurality of analytes of a biological sample, and a method for detecting a plurality of analytes of a biological sample by means of the capture construct.

BACKGROUND

The human proteome contains a significant portion of proteins that are secreted from cells and collectively referred to as the cells' secretome. There is considerable interest in terms of basic and translational research as well as diagnostic applications in obtaining secretion profiles, especially from single cells. A recent study by Uhlén et al. (*Science Signaling*, 26 Nov 2019: Vol. 12, Issue 609, DOI: 10.1126/scisignal.aaz0274) found that the majority of secreted proteins are actually retained intracellularly, i.e. are sorted to intracellular organelles instead of being released from the cell. It is thus of great importance to be able to differentiate between proteins that enter the secretory pathway, but remain intracellular, from the ones that are actually secreted from the cell into the extracellular space or blood stream.

Fluorescence-based assays are commonly used in life science research and diagnostic applications to detect the presence or absence of target analytes. Such target analytes may also be referred to as molecular markers. Molecular markers of interest may be of the group of proteins (proteome level), RNA and in particular mRNA (transcriptome level), DNA (genome level), metabolites (metabolome level), secreted molecules (secretome level), neurotransmitters, hormones and other small molecules of interest.

Citing from Tsai et al. 2020: "Fluorescent cell barcoding (FCB) is a multiplexing technique for high-throughput flow cytometry (FCM). Although powerful in minimizing staining variability, it remains a subjective FCM technique because of inter-operator variability and differences in data analysis" (Tsai et al. J Immunol Methods. 2020 Feb;477: 112667. doi: 10.1016/j.jim.2019.112667.) In FCB up to three dyes are used in four different concentrations to label cells in different wells of a microplate for example by coupling the dyes to reactive amine-groups on the cell surface, which yields different intensities and color combinations. Both the subjectiveness of the technique and inter-operator variability of this method are inherently related to the fact it is based on encoding a part of the information in the hues of dyes, i.e. in intensity variations for example in light-green, green, dark-green, which severely limits the applicability of this technique.

However, no technique allows for capturing a high number of molecular markers, in particular for single cells analysis. Further, techniques for the subsequent detection and analysis of these high number of molecular markers are not known, for example for secretome analysis.

SUMMARY

Embodiments of the present invention provide a capture construct for capturing a plurality of analytes of a biological sample. The capture construct includes a nanostructure backbone, at least a first orientation indicator and a second orientation indicator, and at least a first plurality of capture regions on the nanostructure backbone. Each capture region includes at least one affinity capture reagent configured to capture one of the plurality of analytes.

BRIEF DESCRIPTION OF THE DRAWINGS

Subject matter of the present disclosure will be described in even greater detail below based on the exemplary figures. All features described and/or illustrated herein can be used alone or combined in different combinations. The features and advantages of various embodiments will become apparent by reading the following detailed description with reference to the attached drawings, which illustrate the following.

DETAILED DESCRIPTION

Figure 1:
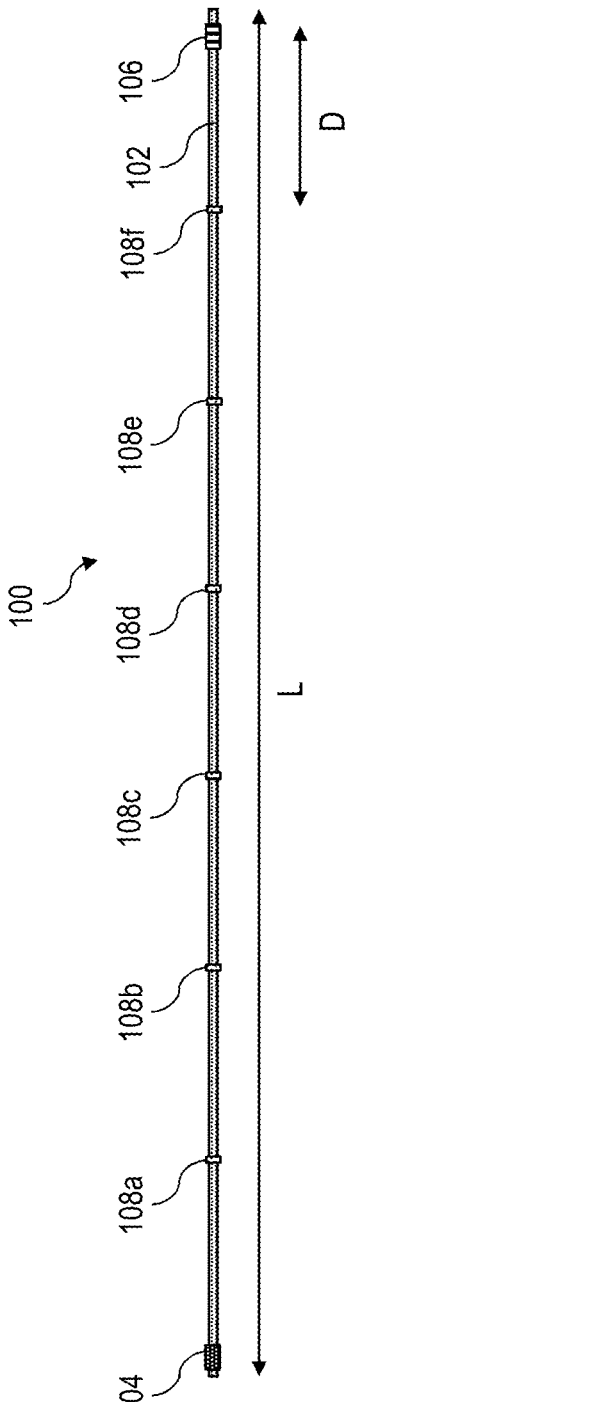
FIG. 1 shows a schematic view of a first embodiment of a capture construct.

Embodiments of the present invention provide a capture construct and a method for capturing a plurality of analytes of a biological sample, which enable capturing of large number analytes in a compact space.

In a first aspect, a capture construct is provided for capturing a plurality of analytes of a biological sample. The capture construct comprises a nanostructure backbone, at least a first orientation indicator and a second orientation indicator, and at least a first plurality of capture regions on the nanostructure backbone, each capture region comprising at least one affinity capture reagent configured to capture one of the analytes. The capture construct enables capturing the plurality of analytes at predetermined positions, the capture regions, on the nanostructure. Further, the capture construct enables capturing the analytes at a high density. The capturing of the plurality of analytes enables subsequent analysis of the plurality of analytes.

The analytes may be a range of molecules. For example, an analyte may be a chemical species such as a metabolic product of the biological sample, or a cell signalling molecule of the biological sample. Further, the analyte may be a protein or peptide of the biological sample, such as a particular enzyme. Further, the analyte may be a hormone or a neurotransmitter. Further, the analyte may be a cell expressing a certain cell-surface protein or a specific combination of cell surface proteins. Further, the analyte may be a cell expressing a certain cell-surface protein or a specific combination of cell surface proteins with a certain glycosylation pattern. Further, the analyte may be a bacterium, an archaeon, a fungus (e.g. a yeast), or a virus. Further, the analyte may be a toxin or a heavy metal. Even further, the analyte may be a nucleic acid molecule, such as DNA or RNA, with a particular nucleic acid sequence.

In particular, the analyte may be secreted by the biological sample, thus, enabling the capture of at least part of the secretome of the biological sample. Each affinity capture reagent may be configured to capture or bind to specifically one of the analytes. Each one of the first plurality of the capture regions may comprise at least one affinity capture reagent attached to the nanostructure backbone in that capture region and configured to specifically bind to or capture one of the analytes. In other words, the capture construct may be configured to such that each analyte is being captured in a particular one of the first capture regions. The capture regions may also be called capture bands. The capture construct may also be called nanoarray.

The biological sample may be a multicellular structure such as a cluster of live cells in particular a spheroid, or a single cell, enabling single cell analysis.

The first orientation indicator and the second orientation indicator may be, for example, fluorescent dyes attached to the nanostructure backbone. The orientation indicators enable determining the spatial orientation or the directionality of the capture construct, in particular the nanostructure backbone. In this way, the orientation indicators enable spatial encoding. This means, different positions on the nanostructure backbone may be assigned to capture bands or capture regions that have reactivities to distinct analytes.

Preferably, the nanostructure backbone comprises nucleic acids. For example, the nanostructure backbone may comprise DNA, RNA and/or LNA. In particular, the nanostructure backbone may comprise DNA origami. These DNA origami structures may range in size from a few nanometres into the micron range. For the fabrication of such DNA origami-based structures longer DNA molecules (scaffold strands) are folded at precisely identified positions by so called staple strands. The DNA origami may be designed to provide a self-assembly nanostructure backbone of a particular predetermined shape. This enables an easy and reproducible synthesis and assembly of the backbone. Staple strands may be position-selectively functionalised. The positional resolution in this case is limited by the size of a nucleotide, which is in the range of a nanometre or below. This has been exploited in the prior art to generate fluorescent standards, wherein fluorescent dyes are connected to precisely located bands on the DNA origami. These standards are known as "nanoruler" and are used for the calibration of imaging systems like confocal or super resolution microscopes (e.g. STED), for example, as disclosed by US2014/0057805 A1.

The DNA origami provides a scaffold for the affinity capture reagents. Preferably, the DNA origami structure comprises at least one scaffold strand and multiple staple strands, wherein the staple strands are complementary to at least parts of the scaffold strand and configured to bring the scaffold strand into a predetermined conformation. In particular, the strands are oligonucleotides. This enables generating nanostructure backbones with predetermined two-or three-dimensional shapes that can self-assemble. Further, this enables the site-specific placement of capture regions on the backbone. Preferably, the affinity capture reagents of the capture regions may be attached to staple strands of the nanostructure backbone at predetermined positions. Staple strands allow the spatially precise functionalisation of the DNA origami at their respective locations on the DNA origami. Thus, each capture region may be located along the nanostructure backbone at a particular staple strand or group of staple strands that are in close proximity. Since the staple strands are located at predetermined positions the positions of the capture regions may equally be predetermined.

It may be preferred, that the affinity capture reagents are selected from an antibody, an antibody fragment such as a single-domain antibody, an aptamer, a peptide, an oligonucleotide, an aptamer, a drug, and/or a toxin. This enables capturing a large variety of analytes with the affinity capture reagents. For example, the analyte may be a protein and the affinity capture reagent may be an antibody. In this case, the antibody may capture the protein by binding to a specific binding site or epitope of the protein. Generally, the affinity capture reagents of a particular capture region may bind to at least one particular binding site of the respective analyte.

In a preferred embodiment, the capture construct comprises a first plurality of affinity reporter reagents, each affinity reporter reagent comprising a first reporter tag and configured to attach to one of the analytes, wherein the first reporter tag is readable, to determine whether or not the respective analyte is captured by the respective affinity capture reagent. This enables determining the presence of a particular analyte by means of the capture construct. Since the capture construct comprises the first plurality of capture regions, a plurality of particular analytes may be captured and their presence determined. Similarly to the affinity capture reagents, each affinity reporter reagent may be configured to capture or bind to specifically one of the analytes. Therefore, each first capture region may comprise at least one affinity reporter reagent configured to specifically bind to one of the analytes associated with one of the first plurality of capture regions. Thus, for each target analyte one capture region with specific affinity capture reagents and specific affinity reporter reagents is provided.

Preferably, the affinity reporter reagents are selected from an antibody, an antibody fragment such as a single-domain antibody, an aptamer, a peptide, an oligonucleotide, an aptamer, a drug, and/or a toxin. This enables capturing and reporting a large variety of analytes with the capture construct. Generally, the affinity reporter reagents of a particular capture region may bind to at least one particular binding site of the respective analyte.

In an embodiment, the reporter tag, in particular the first reporter tag, is optically readable. For example, the reporter tag may comprise a fluorescent dye that is optically detectable. This enables determining by means of a microscope, in particular by imaging with a microscope, whether or not an analyte is captured by the respective affinity capture reagent and the respective affinity reporter reagent with its associated reporter tag is bound to that analyte.

Preferably, the reporter tag, in particular the first reporter tag, is an oligonucleotide and readable by sequencing. This enables determining, whether or not an analyte is captured by the respective affinity capture reagent and the respective affinity reporter reagent with its associated reporter tag is bound to that analyte.

Preferably, the affinity capture reagents are bound to the nanostructure backbone, or the affinity capture reagents of a particular one of the capture regions comprise an oligonucleotide and the respective capture region comprises a complementary oligonucleotide to bind to the oligonucleotide of the affinity capture reagent.

In a preferred embodiment, the affinity capture reagents are covalently bound to the nanostructure backbone, or the affinity capture reagents of a particular one of the capture regions comprise an oligonucleotide and the respective capture region comprises a complementary oligonucleotide to bind to the oligonucleotide of the affinity capture reagent. This enables easy assembly of the capture construct.

The complementary oligonucleotide may be part of the nanostructure backbone, preferably the staple strands, in particular when the nanostructure backbone comprises nucleic acids. For example, each capture region of the nanostructure backbone may have complementary oligonucleotides only complementary to the oligonucleotides of the affinity capture reagent of the respective capture region. When adding the affinity capture reagents to the nanostructure backbone, the affinity capture reagents then only bind to the corresponding complementary oligonucleotide of the respective capture region.

Examples of directly attaching or linking the affinity capture reagents to the staple strands, which enables a position-selective attachment to the nanostructure backbone, include direct chemical coupling through, for example, click chemistry reactions (e.g. Azide-Alkine) or through high-affinity interactions such as biotin-Streptavidin. In the latter case biotinylated staple strands and streptavidin-conjugated affinity capture reagents such as antibodies may be used.

Preferably, the nanostructure backbone comprises at least a second plurality of capture regions, each second capture region comprising at least one affinity capture reagent configured to capture one of the analytes. This enables a dense arrangement of capture regions on the capture construct.

In a preferred embodiment, the capture construct further comprises a second plurality of affinity reporter reagents, each affinity reporter reagent comprising a second reporter tag and configured to attach to one of the analytes, wherein the second reporter tag is readable, to determine whether or not the respective analyte is captured by the respective affinity capture reagent. This enables a dense arrangement of capture regions on the capture construct. In particular, the second reporter tag is optically readable or readable by sequencing. Further, the second plurality of affinity reporter reagents may, in particular, bind to analytes, which are bound to one of the second plurality of capture regions.

Preferably, the nanostructure backbone extends linearly in one dimension and the first orientation indicator and the second orientation indicator are spaced apart from each other, or arranged on opposite ends of the nanostructure backbone. This enables determining the orientation of the capture construct. The orientation indicators may be fluorescent dyes, for example. In particular, the first orientation indicator and the second orientation indicator have different properties, such as excitation wavelength, fluorescence emission wavelength, and/or fluorescence lifetime.

In an embodiment, the nanostructure backbone extends in two dimensions or three dimensions and the nanostructure backbone comprises at least a third orientation indicator. This enables determining the orientation of the capture construct.

It is preferred, that the largest spatial extent of the nanostructure backbone is in a range from 1 nm to 10000 nm, preferably in a range from 0.1 µm to 5 µm, more preferably in a range from 0.1 µm to 1 µm. This enables a compact capture construct.

Preferably, the capture regions of the first plurality of capture regions are spaced apart from each other in a range from 1 nm to 2000 nm, preferably in a range from 200 nm to 1000 nm. This enables a dense arrangement of capture regions on the nanostructure backbone.

In an embodiment, the capture regions of the first plurality of capture regions are spaced apart from the capture regions of the second plurality of capture regions in a range from 0.1 nm to 500 nm, preferably in a range from 1 nm to 100 nm. This enables a dense arrangement of capture regions on the nanostructure backbone.

Preferably, the reporter tags comprise fluorophores, in particular with differing excitation wavelength, fluorescence emission wavelength, and/or fluorescence lifetime characteristics. In particular, the first reporter tags and the second reporter tags differ in their excitation wavelength, fluorescence emission wavelength, and/or fluorescence lifetime characteristics. This enables arranging capture regions close together. In particular, this enables arranging a capture region of the first plurality of capture regions in a distance to a capture region of the second plurality of capture regions that is within the diffraction limit.

In a preferred embodiment, the affinity capture reagents of at least one of the capture regions are configured to bind one of the analytes at a single binding site of the analyte. This enables binding of the analyte with high sensitivity and specificity. For example, the analyte may be a protein and the affinity capture reagent may be an antibody. In this case, the antibody may capture the protein by binding to a specific binding site or epitope of the protein.

In an embodiment, at least one capture region comprises a first set of affinity capture reagents and a second set of affinity capture reagents, and wherein the first set of affinity capture reagent is configured to bind one of the analytes at a first binding site of the one analyte and the second set of affinity capture reagents is configured to bind the one of the analytes at a second binding site of the one analyte. This enables binding of the analyte with high avidity. For example, a capture region may be configured such that an analyte may be bound at several different binding sites with the associated affinity capture reagents being specific to one of the binding sites and the capture region comprising affinity capture reagents for each of the binding sites. In an alternative example, an analyte may comprise several of the same binding site and the capture region may be configured such that the analyte may be bound by several of the associated affinity capture reagents specific to the one binding site.

In an embodiment, the first set of affinity capture reagents comprises first capture reagent dyes and the second set of affinity capture reagents comprises second capture reagent dyes. In particular the capture reagent dyes are fluorophores.

It may be preferred, that the first capture reagent dyes and the second capture reagent dyes are configured to be brought into proximity when the one analyte is captured by one of the affinity capture reagents of the first set of affinity capture reagents and by one of the affinity capture reagents of the second set of affinity capture reagents, and wherein the proximity enables an energy transfer between the respective capture reagent dyes. In particular, the proximity enables the formation of a FRET (fluorescence resonance energy transfer) pair or FRET n-tuples between the respective capture reagent dyes. This enables high specificity when capturing and detecting analytes.

Preferably, the capture construct and the biological sample are embedded in or attached to a polymeric compound, in particular a hydrogel. This keeps the capture construct and the biological sample in close proximity and enables easy handling of the biological sample with the capture construct.

In a further aspect, a method is provided for detecting a plurality of analytes of a biological sample, the method comprising the following steps: Incubation of the biological sample in the presence of at least one capture construct; Acquiring a readout of at least the one capture construct, in particular the capture regions; Determining whether or not the respective analytes are captured by the respective affinity capture reagent.

Terms

In the sense of this document the following terms are used in the following way:

"Sample": In the sense of this document "sample" may refer to a biological sample which may also be named a biological specimen including, for example blood, serum, plasma, tissue, bodily fluids (e.g. lymph, saliva, semen, interstitial fluid, cerebrospinal fluid), feces, solid biopsy, liquid biopsy, explants, whole embryos (e.g. zebrafish, *Drosophila*), entire model organisms (e.g. zebrafish larvae, *Drosophila* embryos, *C. elegans*), cells (e.g. prokaryotes, eukaryotes, archea), multicellular organisms (e.g. Volvox), suspension cell cultures, monolayer cell cultures, 3D cell cultures (e.g. spheroids, tumoroids, organoids derived from various organs such as intestine, brain, heart, liver, etc.), a lysate of any of the aforementioned, a virus. In the sense of this document "sample" may further refer to a volume surrounding a biological sample. For example, in assays, where secreted proteins such as growth factors, extracellular matrix constituents are being studied, the extracellular environment surrounding a cell up to a certain assay-dependent distance, may also be referred to as the "sample". Specifically, affinity reagents brought into this surrounding volume may be referred to as being "introduced into the sample".

"Affinity reagent": In the sense of this document the term "affinity reagent" and/or "affinity capture reagent" may in particular be an antibody, a single-domain antibody (also known as nanobody), a combination of at least two single-domain antibodies, an aptamer, an oligonucleotide, a morpholino, a PNA complementary to a predetermined RNA, DNA target sequence, a ligand (e.g. a drug or a drug-like molecule), or a toxin, e.g. Phalloidin a toxin that binds to an actin filament. In the sense of this document an affinity reagent may be configured to bind a target molecule or to an analyte with a certain affinity and specificity such that it can be said that the affinity reagent is substantially specific only to the target molecule or predetermined target structure.

"Analyte": In the sense of this document "analyte" or "predetermined target structure" may refer to a target molecule or a target structure or to an analyte, which may, for example, be a protein (e.g. a certain protein), an RNA sequence (e.g. the mRNA of a certain gene), a peptide (e.g. somatostatin), a DNA sequence (e.g. the a genetic locus or element), a metabolite (e.g. lactic acid), a hormone (e.g. estradiol), a neurotransmitter (e.g. dopamine), a vitamin (e.g. cobalamine), a micronutrient (e.g. biotin), a metal ion (e.g. metal and heavy metal ions like Cd(II), Co(II), Pb(II), Hg(II), U(VI)).

"Dye": In the sense of this document the terms "fluorescent dye", "fluorophore", "fluorochrome", "dye" are used interchangeably to denote a fluorescent chemical compound or structure and may be, in particular, one of the following: a fluorescent organic dye, a fluorescent quantum dot, a fluorescent dyad, a fluorescent carbon dot, a graphene quantum dot or another carbon-based fluorescent nanostructure, a fluorescent protein, a fluorescent DNA origami-based nanostructure. From the organic fluorescent dyes in particular derivatives of the following are meant by the term "fluorescent dye": xanthene (e.g. fluorescein, rhodamine, Oregon green, Texas), cyanine (e.g. cyanine, indocarbocyanine, oxacarbocyanine, thiacarbocyanine, merocyanine), squaraine rotaxane derivatives, naphthalene, coumarin, oxadiazole, anthracene (anthraquinones, DRAQ5, DRAQ7, CyTRAK Orange), pyrene (cascade blue), oxazine (Nile red, Nile blue, cresyl violet, oxazine 170), acridine (proflavine, acridine orange, acridine yellow), arylmethine (auramine, crystal violet, malachite green), tetrapyrrole (porphin, phthalocyanine, bilirubin), dipyrromethene (BODIPY, aza-BODIPY), a phosphorescent dye, or a luminescent dye. The following trademark groups designated commercially available fluorescent dyes, which may include dyes belonging to different chemical families CF dye (Biotium), DRAQ and CyTRAK probes (BioStatus), BODIPY (Invitrogen), Ever-Fluor (Setareh Biotech), Alexa Fluor (Invitrogen), Bella Fluore (Setareh Biotech), DyLight Fluor (Thermo Scientific), Atto and Tracy (Sigma-Aldrich), FluoProbes (Interchim), Abberior Dyes (Abberior Dyes), Dy and MegaStokes Dyes (Dyomics), Sulfo Cy dyes (Cyandye), HiLyte Fluor (AnaSpec), Seta, SeTau and Square Dyes (SETA BioMedicals), Quasar and Cal Fluor dyes (Biosearch Technologies), SureLight Dyes (Columbia Biosciences), Vio Dyes (Milteny Biotec) [list modified from: https://en.wikipedia.org/wiki/Fluorophore]. From the group of fluorescent proteins in particular the members of the green fluorescent protein (GFP) family including GFP and GFP-like proteins (e.g DsRed, TagRFP) and their (monomerized) derivatives (e.g., EBFP, ECFP, EYFP, Cerulaen, mTurquoise2, YFP, EYFP, mCitrine, Venus, YPet, Superfolder GFP, mCherry, mPlum) are meant by the term "fluorescent dye". Further, from the group of fluorescent proteins the term "fluorescent dye" may include fluorescent proteins, whose absorbance or emission characteristics change upon binding of ligand like for example BFPmsI or in response to changes in the environment like for example redox-sensitive roGFP or pH-sensitive variants. Further, from the group of fluorescent proteins the term "fluorescent dye" may include derivative of cyanobacterial phycobiliprotein small ultra red fluorescent protein smURFP as well as fluorescent protein nanoparticles that can be derived from smURFP. An overview of fluorescent proteins can be found in Rodriguez et al 2017 in Trends Biochem Sci. 2017 Feb; 42 (2): 111-129. The term "fluorescent dye" may further refer to a fluorescent quantum dot. The term "fluorescent dye" may further refer to fluorescent carbon dot, a fluorescent graphene quantum dot, a fluorescent carbon-based nanostructure as described in Yan et al. 2019 in Microchimica Acta (2019) 186: 583 and Iravani and Varma 2020 in Environ Chem Lett. 2020 Mar 10: 1-25. The term "fluorescent dye" may further refer to a fluorescent polymer dot (Pdot) or nanodiamond. The term "fluorescent dye" may further refer to a fluorescent dyad, like for example a dyad of a perylene antenna and a triangelium emitter as described in Kacenauskaite et al. 2021 J. Am. Chem. Soc. 2021, 143, 1377-1385. The term "fluorescent dye" may further refer to an organic dye, a dyad, a quantum dot, a polymer dot, a graphene dot, a carbon-based nanostructure, a DNA origami-based nanostructure, a nanoruler, a polymer bead with incorporated dyes, a fluorescent protein, an inorganic fluorescent dye, a SMILE, or a microcapsule filled with any of the aforementioned. The term "fluorescent dye" may further refer to a FRET-pair having at least one fluorescent dye as FRET donor and at least one fluorescent dyes as a FRET acceptor, or a FRET-triple, which is used to generate a three component Förster resonance energy transfer. In particular, the FRET-pair or FRET-triplet may be connected by a complementary linker or by a linker. The term "fluorescent dye" may further refer to a FRET n-tuple of physically connected dyes.

"Readout device": The term "readout device" may refer to a device used to perform fluorescence multicolour reading or imaging. A readout device typically includes at least one excitation light source, a detection system including at least one detection channel and may further contain filters and/or dispersive optical elements such as prisms and/or gratings to route excitation light to the sample and/or to route emission light from the sample onto to a detector or onto an appropriate area of the detector. The detection system may comprise several detection channels, may be a spectral detector detecting multiple bands of the spectrum in parallel, or a hyperspectral detector detecting a contiguous part of the spectrum. The detection system contains at least one detector, which may be a point-detector (e.g. a photomultiplier, an avalanche diode, a hybrid detector), an array-detector, a camera, hyperspectral camera. The detection system may record intensities per channel as is typically the case in cytometers or may be an imaging detection system that records images as in the case of plate readers or microscopes. A readout device with one detector channel, for example a camera or a photomultiplier, may generate readouts with multiple detection channels using, for example, different excitation and emission bands.

"Oligonucleotide": in the sense of this document may refer to DNA, RNA, peptide nucleic acid, morpholino or locked nucleic acid, glycol nucleic acid, threose nucleic acid, hexitol nucleic acid or another form of artificial nucleic acid.

"Point spread function": The term "point spread function" may be used to denote the main maximum of the point spread function and unless otherwise denoted the term refers to the effective point spread function (PSF) of the imaging system, which is generally elliptical, i.e. the lateral resolution is better than the axial resolution, but may approach an almost spherical shape as more views are acquired from preferably equidistant angles.

FIG. 1 shows a linear, rod-like nanoarray 100 with a linear nanostructure backbone 102, a first orientation indicator 104, a second orientation indicator 106, a first plurality of capture regions 108a to 108f.

Preferably, the nanostructure backbone 102 comprises nucleic acids. In particular, the nanostructure backbone 102 is a DNA-origami based, which allows generating arbitrary, stable two-and three-dimensional shapes.

The orientation indicators 104, 106 may be used to determine the orientation, directionality or polarity of the nanoarray 100. The orientation indicators 104, 106 may comprise a dye, in particular a fluorescent dye, such as fluorescein or a fluorescent protein. In addition, the dye of the first orientation indicator 104 has different characteristics than the dye of the second orientation indicator 106. The characteristics may include fluorescent emission characteristics, excitation characteristics or lifetime characteristics. This enables differentiating between the first and the second orientation indicators 104, 106 in an optical readout of the nanoarray 100, for example generated by a microscope, a cytometer, or an imaging cytometer. The orientation indicators 104, 106 are arranged spaced apart from each other. Preferably each orientation indicator 104, 106 is arranged on the backbone 102 at opposite ends. Thus, the first and second orientation indicators 104, 106 enable differentiating between a first end and a second end of the backbone 102 and therefore the nanoarray 100. Ultimately, this enables determining the orientation, directionality or polarity of the nanoarray 100, for example from the first orientation indicator 104 on the first end to the second orientation indicator 106 on the second end. Based on the directionality, the orientation indicators 104, 106 generate a relative coordinate system for the nanoarray 100, on which each capture region 108a to 108f may be placed. In case of the linear nanoarray 100, each capture region 108a to 108f is placed at a unique location on the backbone 102. Each capture region 108a to 108f may be assigned an index n with n=1, 2, 3, . . . , based on the unique location of the respective capture region 108a to 108f. In addition, the orientation indicators 104, 106 and their corresponding unique dye characteristics may be used to identify the particular capture construct 100 from a variety of capture construct with orientation indicators with different dye characteristics.

Each capture region 108a to 108f is configured to capture an analyte of a biological sample. The capture regions 108a to 108f comprise affinity capture reagents with each capture region 108a to 108f comprising affinity capture reagents that bind a particular analyte. Thus, the nanoarray 100 comprises six capture regions 108a to 108f to capture six different analytes. In addition, the first and second orientation indicators 104, 106 may be used as capture regions, which would result in the nanoarray 100 capturing eight different analytes.

As indicated in FIG. 1, the placing of the capture regions 108a to 108f and orientation indicators 104, 106 may be such that their distance to each other (D) is in the range of 500 nm, which leads to the backbone 102 having a length L of approximately 3.5 μm. The spacing D may be chosen depending on the resolving power of a readout device used to read out the capture regions 108a to 108f and may be in the range of 1 nm to 5 nm, 10 nm to 25 nm, 50 nm to 100 nm, 100 nm to 250 nm, 250 nm to 500 nm, or 500 nm to 1000 nm. The preferable ranges correspond to the lateral resolution achievable with different microscopic modalities such as for example single molecule localization microscopy (1 nm to 25 nm), structured illumination and STED microscopy (50 nm to 100 nm), high NA (numerical aperture) light microscopy (around 200 nm), and low NA light microscopy (around 500 nm).

In order to read out the capture regions 108a to 108f, generally, the orientation indicators 104, 106 are read out as well. This enables identifying the individual capture regions 108a to 108f in the readout based on the index n, as described above.

Figure 2:
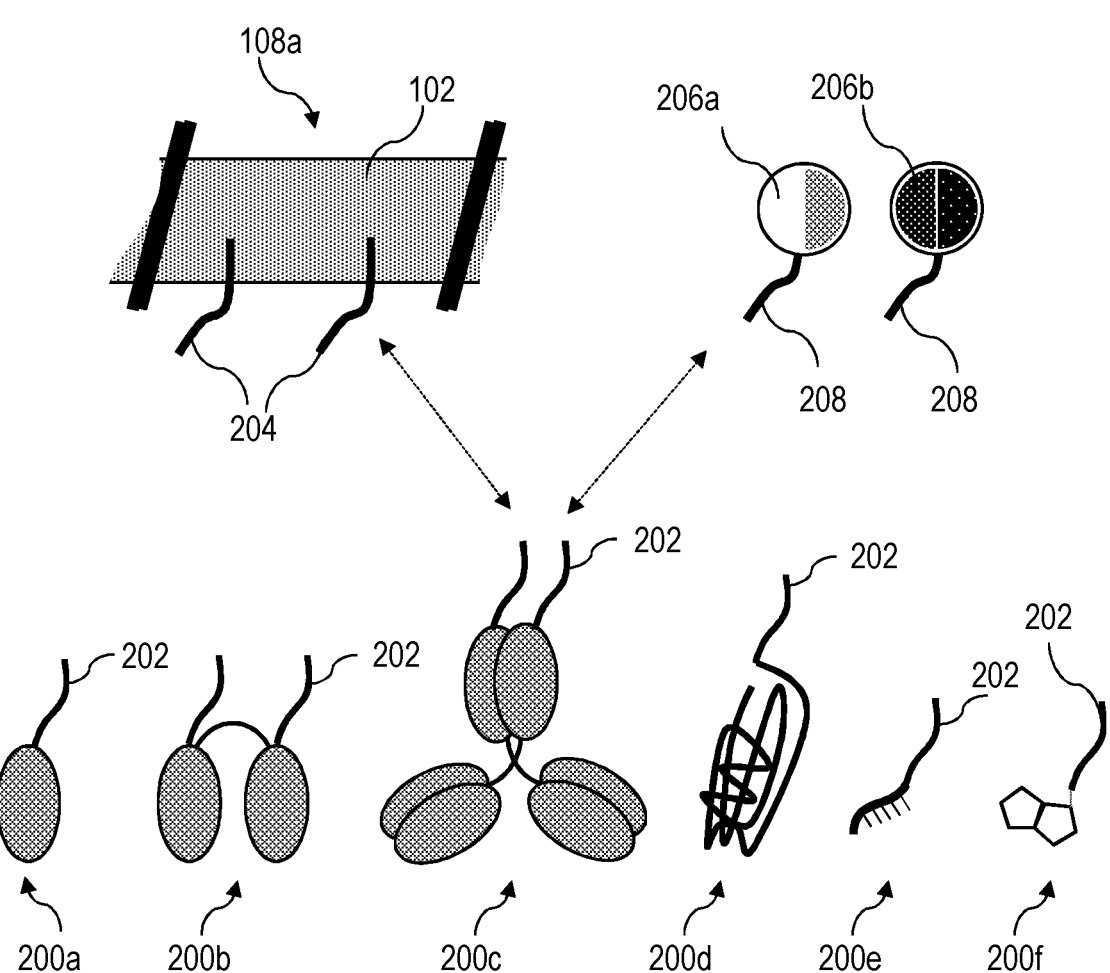
FIG. 2 shows schematically different affinity reagents according to some embodiments.

FIG. 2 shows schematically different affinity reagents 200a to 200f. The affinity reagents 200a to 200f are, for example, single domain antibodies 200a, dimerised single domain antibodies 200b, antibodies 200c, aptamers 200d, oligonucleotide-based affinity reagents 200e, or small molecule-based affinity reagents 200f. These affinity reagents 200a to 200f may be used as the affinity capture reagents of one of the capture regions 108a to 108f. Here, the capture region 108a is exemplarily shown.

In a preferred embodiment, the affinity capture reagents comprise oligonucleotide tags 202. Further the capture regions 108a to 108f may comprise corresponding complementary oligonucleotide tags 204, in particular, in case the backbone 102 is a DNA origami-based. The oligonucleotide tags 204 may in that case be included in the backbone 102 when designing and constructing the DNA origami backbone 102 such that the tags 204 are accessible on the structure or protrude from the structure at the specific locations of the capture regions 108a to 108f. For example, the staple strands of the DNA origami may comprise the tags 204. Since the staple strands are at known predetermined locations of the DNA origami, the affinity capture reagents may be attached to these known predetermined locations to form the capture regions. Complementary tags 202, 204 may be used to assemble the capture construct. For example, the backbone 102 may be constructed with unique tags 204 for each capture region 108a to 108f and the tags 204 chosen such that they correspond to the unique complementary tags 202 of the affinity capture reagents of each capture region 108a to 108f. Thus, the capture regions 108a to 108f are an area of the backbone 102, in which affinity capture reagents are bound to the backbone.

Alternatively, the affinity capture reagents may be covalently attached to the backbone 102.

Further, the affinity reagents 200a to 200f may be used to generate affinity reporter reagents. In particular, this may be achieved by attaching a dye 206a, 206b to the affinity reagent 200a to 200f by complementary oligonucleotide tags 202, 208, as described above. The dyes 206a, 206b may be fluorescent dyes, such as fluorescein or a fluorescent protein. In addition, the dyes 206a, 206b may have different characteristics such as fluorescent emission characteristics, excitation characteristics or lifetime characteristics. The dyes 206a, 206b comprise the oligonucleotide tag 208 which may be attached to the complementary oligonucleotide tags 202 of the affinity reagents 200a to 200b to provide a corresponding affinity reporter reagent.

The use of oligonucleotide tags 202, 204, 208 enables creating libraries of affinity reagents 200a to 200b that can be mixed and matched according to a user's requirements to result in required affinity capture reagents and affinity reporter reagents. This enables the flexible and cost-effective assembly of affinity capture reagents on the nanostructures, as well as the assembly of suitable dye-conjugated affinity reporter reagents.

Figure 3:
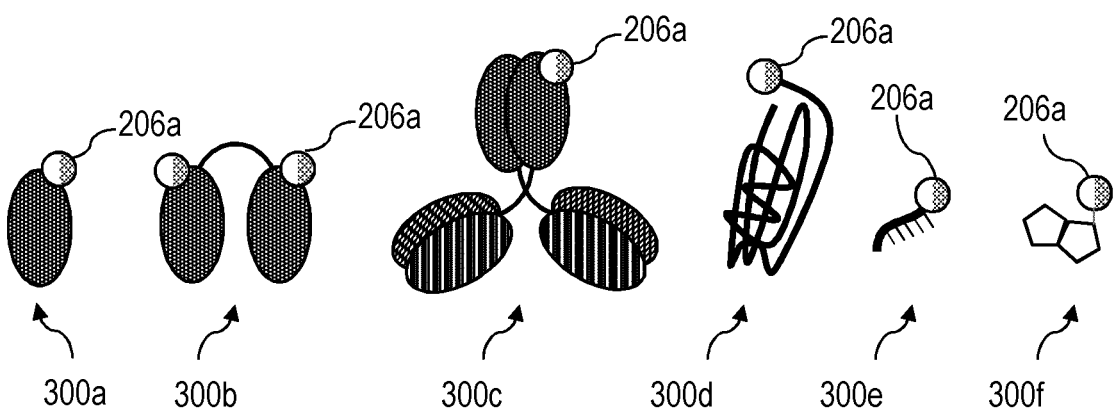
FIG. 3 shows affinity reporter reagents with directly attached dyes according to some embodiments.

Alternatively, FIG. 3 shows affinity reporter reagents 300a to 300f with directly attached dyes 206a, 206b. For example, the affinity reporter reagents 300a to 300f may have covalently attached dyes 206a, 206b.

Figure 4:
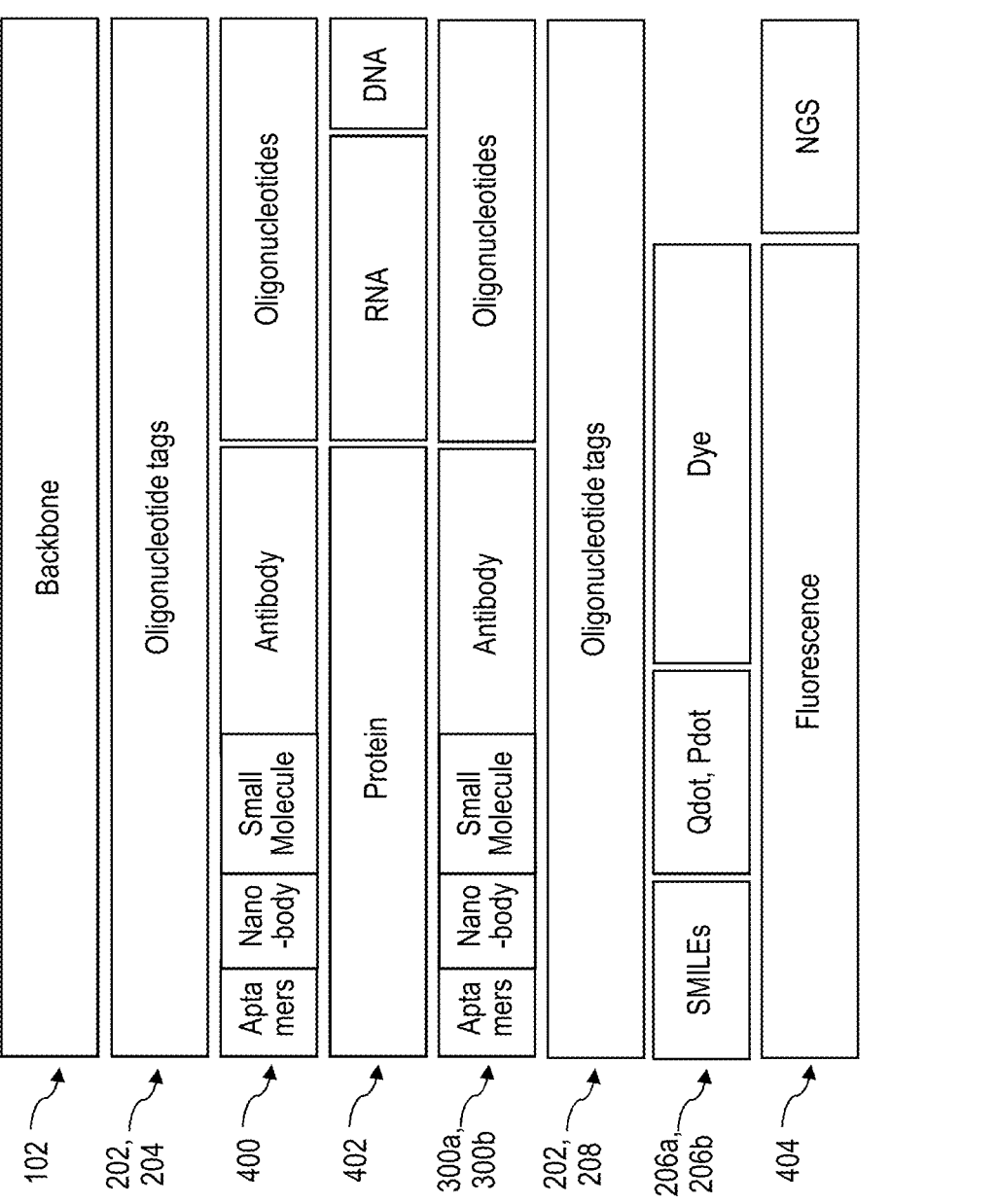
FIG. 4 shows a schematic overview of the elements of the capture construct according to some embodiments.

FIG. 4 shows a schematic overview of the elements of the capture construct 100, in particular of one of the capture regions 108a to 108f. Each capture region 108a to 108f has a plurality of affinity capture reagents 400 attached to the area of the backbone 102. These affinity capture reagents 400 may be attached to the backbone 102 by linkers such as the oligonucleotide tags 202, 204. The affinity capture reagents 400 bind a respective analyte 402. In order to analyse the captured analytes 402, the affinity reporter reagents 300a to 300b may be attached to the analyte 402, the reporter reagents 300a to 300b comprising a dye 206a, 206b, which may be attached by linkers such as the oligonucleotide tags 202, 208. The linkers 202, 204, 208 are optional and may further be photocleavable or enzymatically cleavable, for example, with restriction enzymes, recombinases, endonucleases, CriSPR/CAS, Cre/loxP and similar. The readout 404 may be achieved by (next generation) sequencing (NGS) or fluorescence detection, in order to determine whether or not the analyte is bound to a particular one of the capture regions 108a to 108f. The readout may be achieved by sequencing when the reporter reagent 300a-300f comprises a sequencable oligonucleotide, for example. The individual elements shown in FIG. 4 may be combined, for example, a particular analyte, such as a protein, may be captured by an antibody capture reagent and an antibody fragment reporter reagent may be used, with a fluorescent dye attached, to be read out by a microscope. Alternatively, the capture reagent may be a small molecule and the reporter reagent an antibody fragment.

Figure 5:
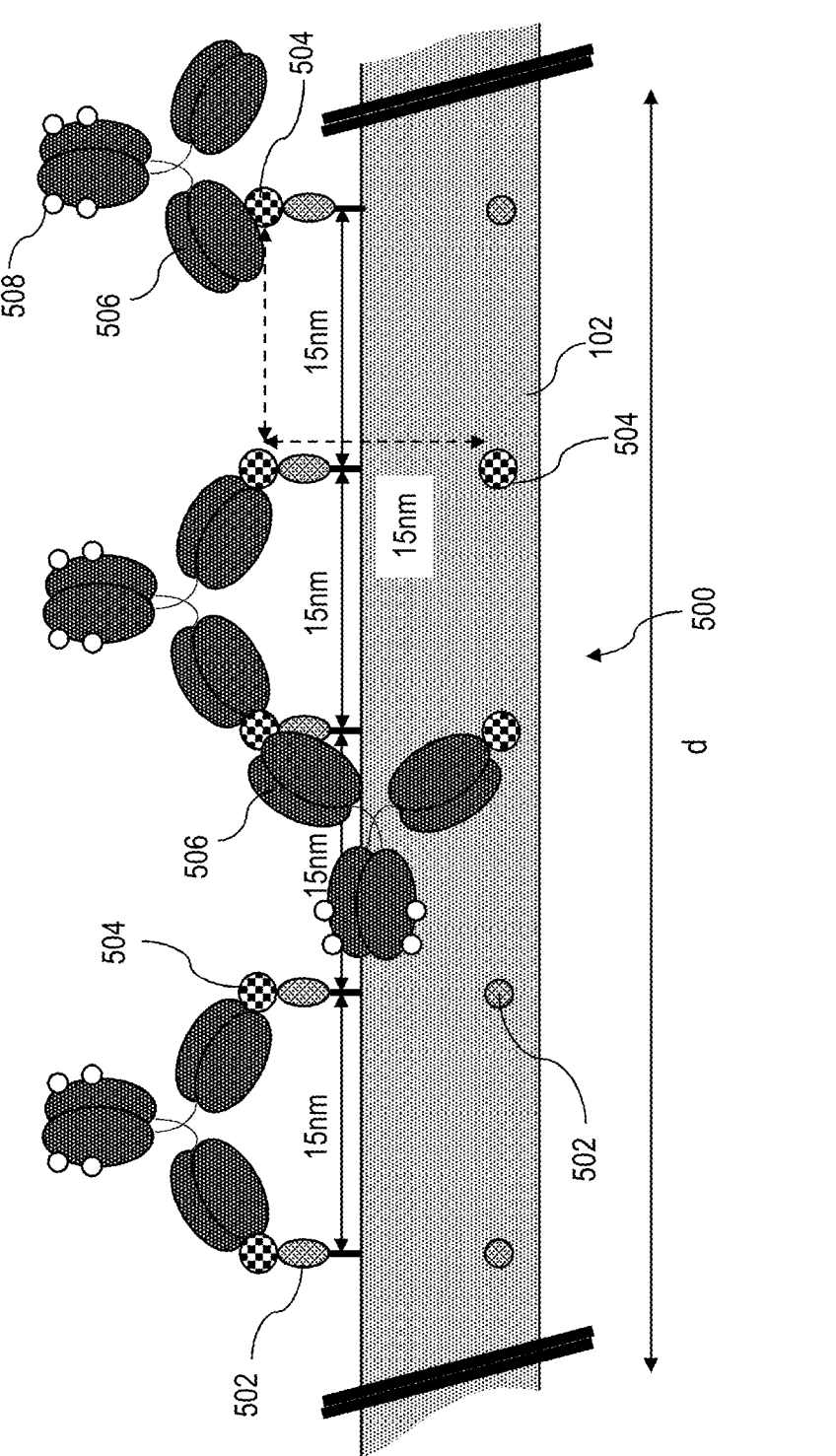
FIG. 5 shows a schematic view of a first embodiment of a capture region.
Figure 6:
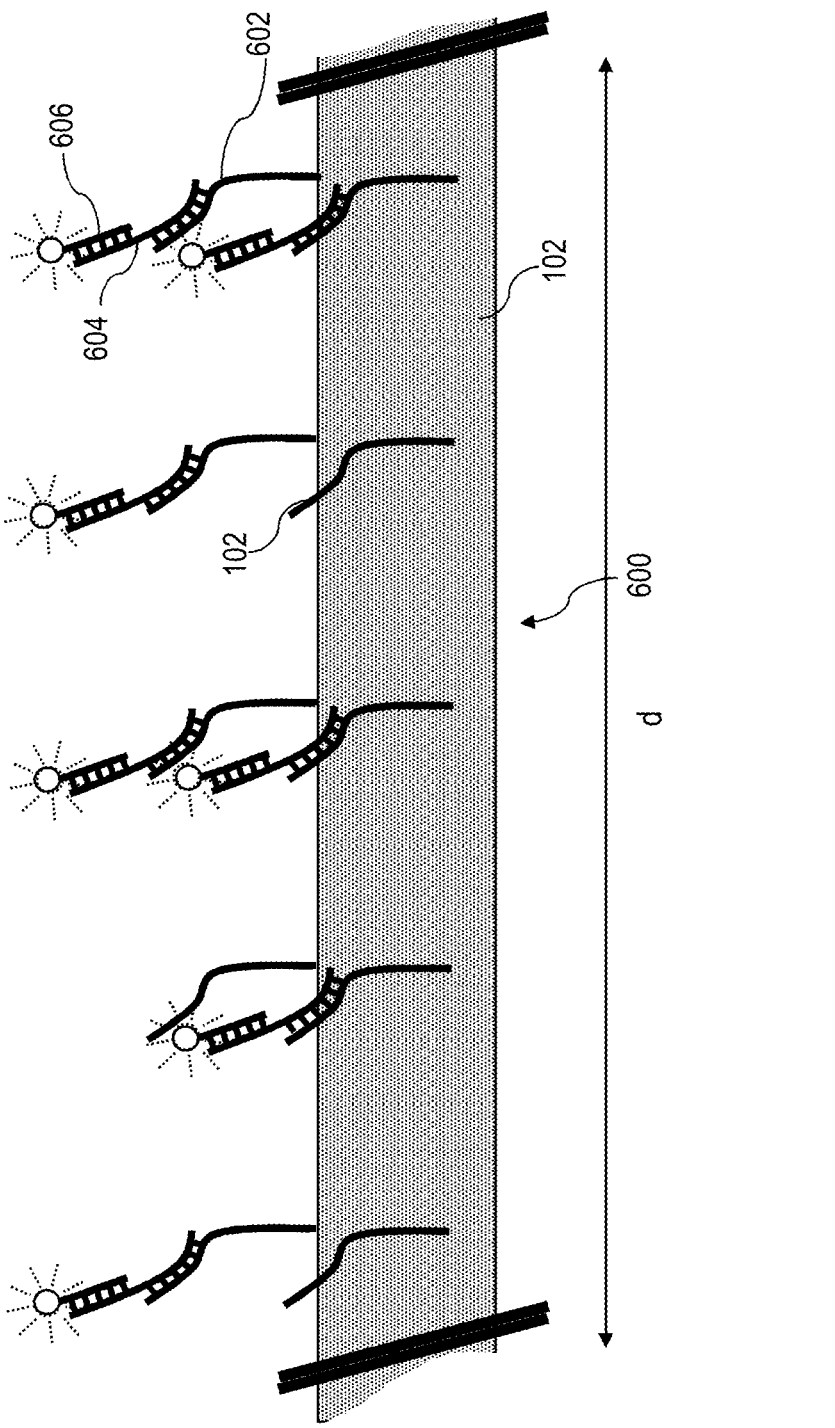
FIG. 6 shows a schematic view of a second embodiment of the capture region.
Figure 7:
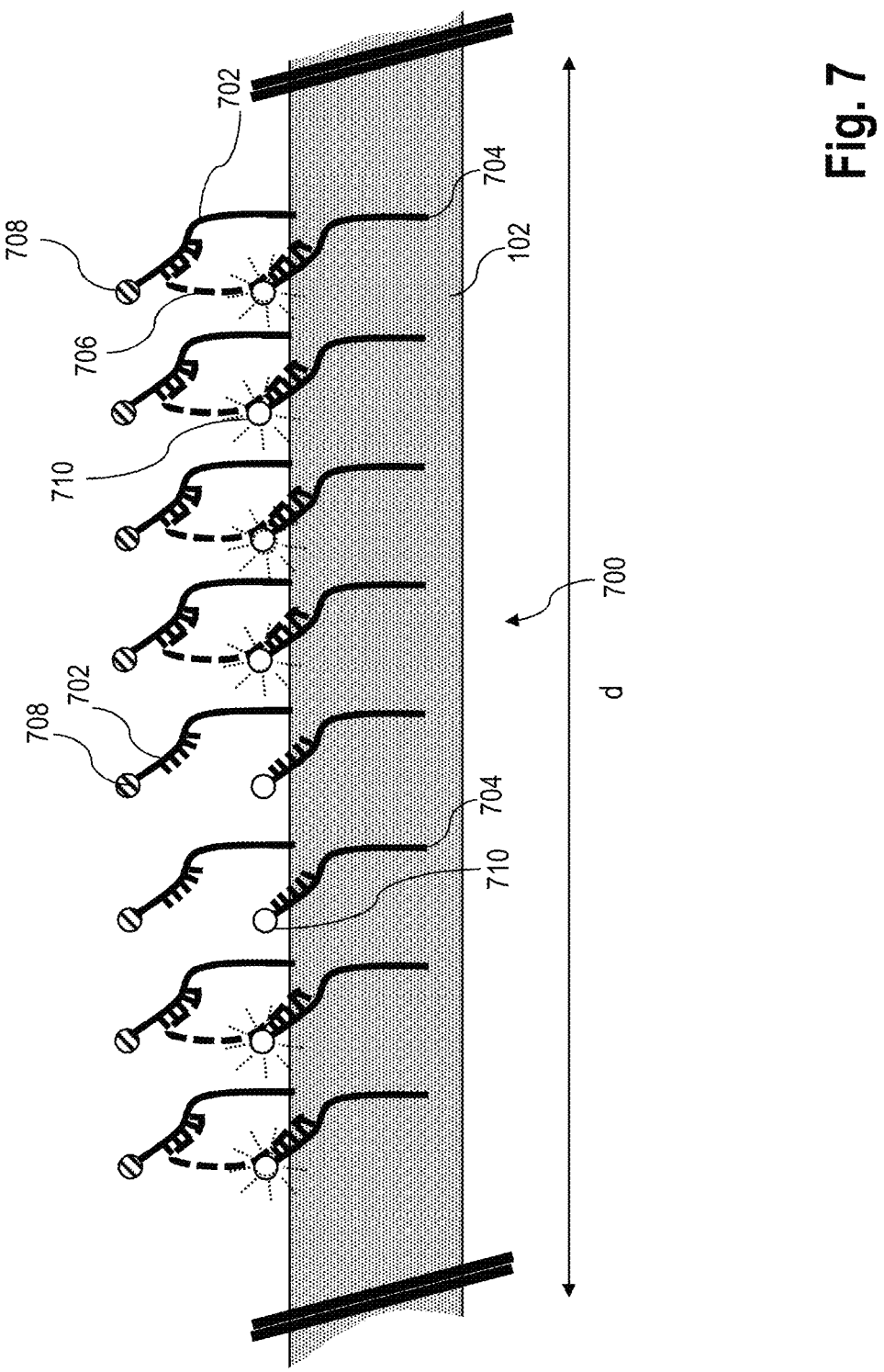
FIG. 7 shows a schematic view of a third embodiment of the capture region.

FIGS. 5 to 7 show specific examples of possible configurations of the capture construct 100, in particular of the capture regions 108a to 108f.

FIG. 5 shows a schematic view of a capture region 500. To the capture region 500 are attached multiple affinity capture reagents 502 in the form of single domain antibodies. The single domain antibodies specifically bind a particular analyte 504 of interest at a first binding site. Thus, the capture region 500 binds the analyte 504 where a capture reagent 502 is attached to the capture region 500.

In order to subsequently determine whether or not the analytes 504 are captured by the capture reagents 502, affinity reporter reagents 506 may be added. The affinity reporter reagents 506, in the form of antibodies, bind to the analyte at least at a second binding site. The affinity reporter reagents 506 comprise dyes 508, such as a fluorescent dye. Thus, the affinity reporter reagents 506 only accumulate at the capture region 500 when the analyte 504 is bound to the capture region 500. The presence of the affinity reporter reagent 506 and thus the analyte 504 may then be read out by the readout device as an optical signal of the dye 508. Only in the case that an optical signal of the dye 508 is detected in the capture region 500, it is determined that the analyte 504 is captured in the capture region 500.

More specifically, FIG. 5 shows additional, optional features of the capture region 500. The use of a small affinity capture reagent 502, in the form of an antibody fragment, enables the spacing of analyte binding sites in a raster that has approximately 15 nm spacing, which corresponds roughly to the distance between the two binding sites, or paratopes, of conventional antibodies and is thus suited to create an avidity effect, which may increase the overall sensitivity of the assay substantially. Further, the three-dimensional arrangement of the affinity capture reagents 502 along and around the circumference of the rod-like backbone 102 increases the density of the binding sites of the affinity capture reagents 502 and consequently the affinity reporter reagents 506. This increases the signal to noise ratio of the optical signal when reading out the capture region 500. Finally, capturing a given analyte with two distinct affinity capture reagents and/or two distinct affinity reporter reagents, preferably each with different epitopes increases specificity of the assay and reduces sterical problems.

FIG. 6 schematically shows a capture region 600 with affinity capture reagents 602 in the form of oligonucleotides. The affinity capture reagent 602 is configured to bind an oligonucleotide analyte 604 comprising a complementary nucleic acid sequence. The analyte 604 bound to the capture reagent 602 may be determined by reading out the presence of an affinity reporter reagent 606 bound to the analyte 604 and comprising a complementary nucleic acid sequence to the analyte 604. The reagents 602, 606 and the analyte 604 may comprise DNA, RNA and/or LNA nucleotides. This enables detection of nucleic acid sequences with high sensitivity. This is advantageous for numerous applications as nucleic acid sequences occur in bodily fluids or can be released from cells following lysis and potentially shearing of the DNA. This embodiment is also advantageous for diagnostic testing in the context of liquid biopsies and their use to detect the presence of cancer. In this case circulating tumor DNA (ctDNA) target sequences may be detected. Further this embodiment is advantageous for diagnostic testing of pathogen infection such as viral or bacterial infections including sepsis testing. Further areas of application are in pathogen detection in food and water quality testing and monitoring.

FIG. 7 schematically shows a capture region 700 with a first set of affinity capture reagents 702 in the form of oligonucleotides and a second set of affinity capture reagents 704 in the form of oligonucleotides. The affinity capture reagents 702, 704 are configured to bind an oligonucleotide analyte 706 at either a first complementary sequence or a second complementary sequence. Further the affinity capture reagents 702, 704 each have a corresponding first dye 708 or second dye 710 attached. When the analyte is bound to one of the affinity capture reagents 702 of the first set and one of the affinity capture reagents 704 of the second set, the first and second dyes 708, 710 of the respective affinity capture reagents 702, 704 are brought into close proximity. When the dyes 708, 710 are in close proximity they form a FRET-pair and a corresponding optical signal may be detected by the readout device. FRET refers to fluorescence resonance energy transfer. This increases the specificity of the detection of the analyte.

Figure 8:
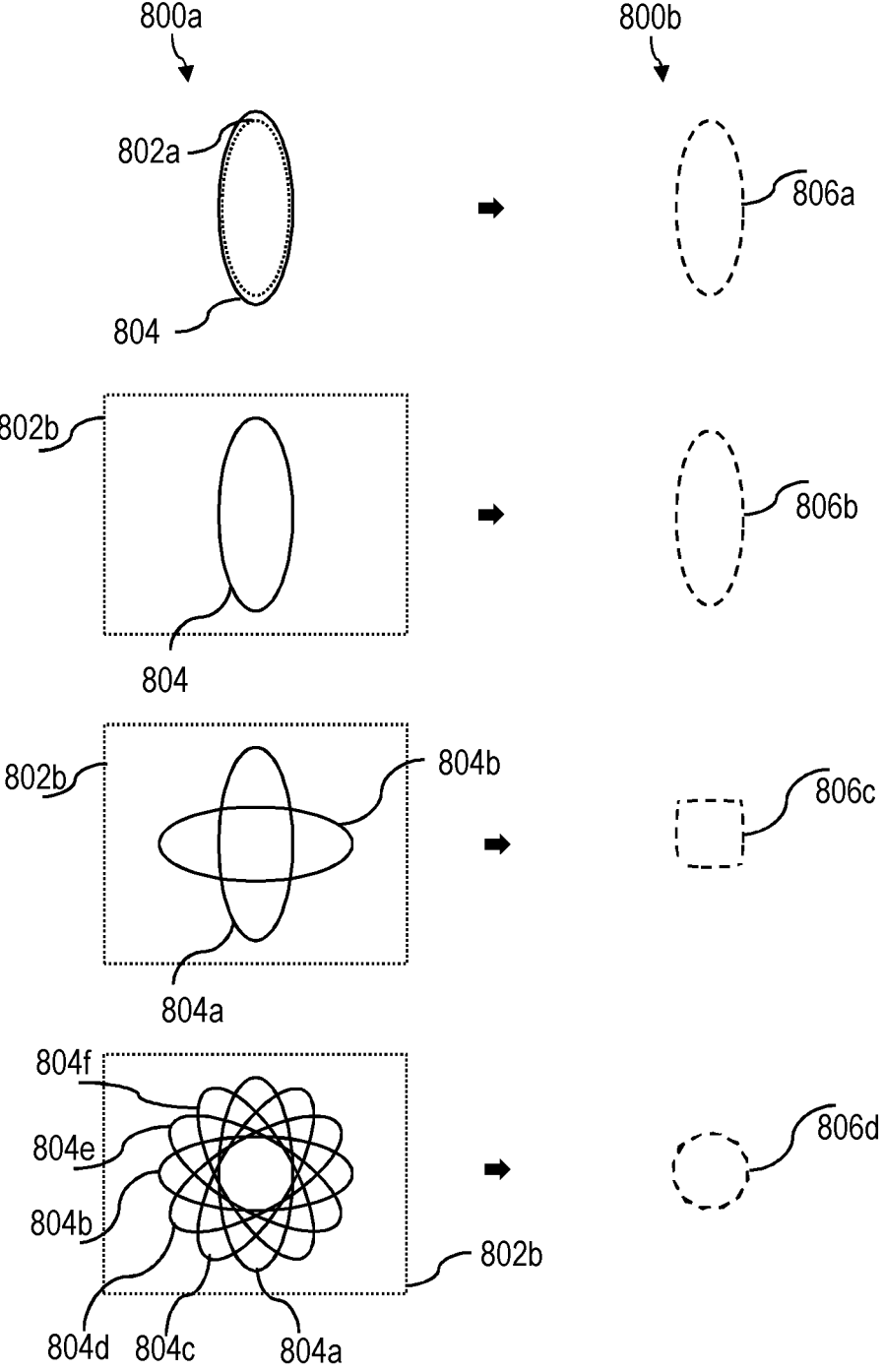
FIG. 8 shows a column of illumination and detection points spread functions and a column of corresponding effective point spread functions according to some embodiments.
Figure 9:
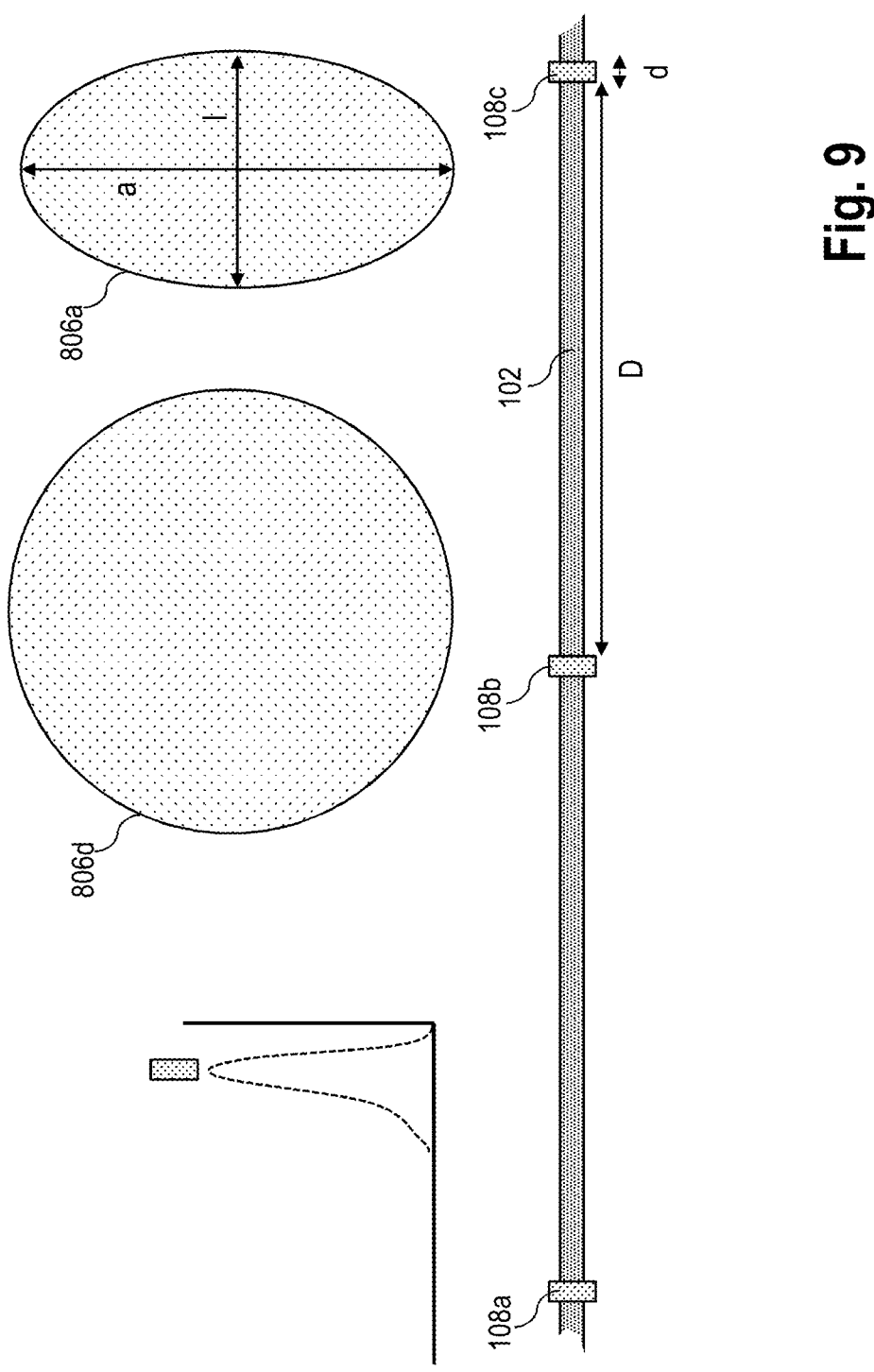
FIG. 9 shows a detailed view of the capture construct according to FIG. 1, according to some embodiments.
Figure 10:
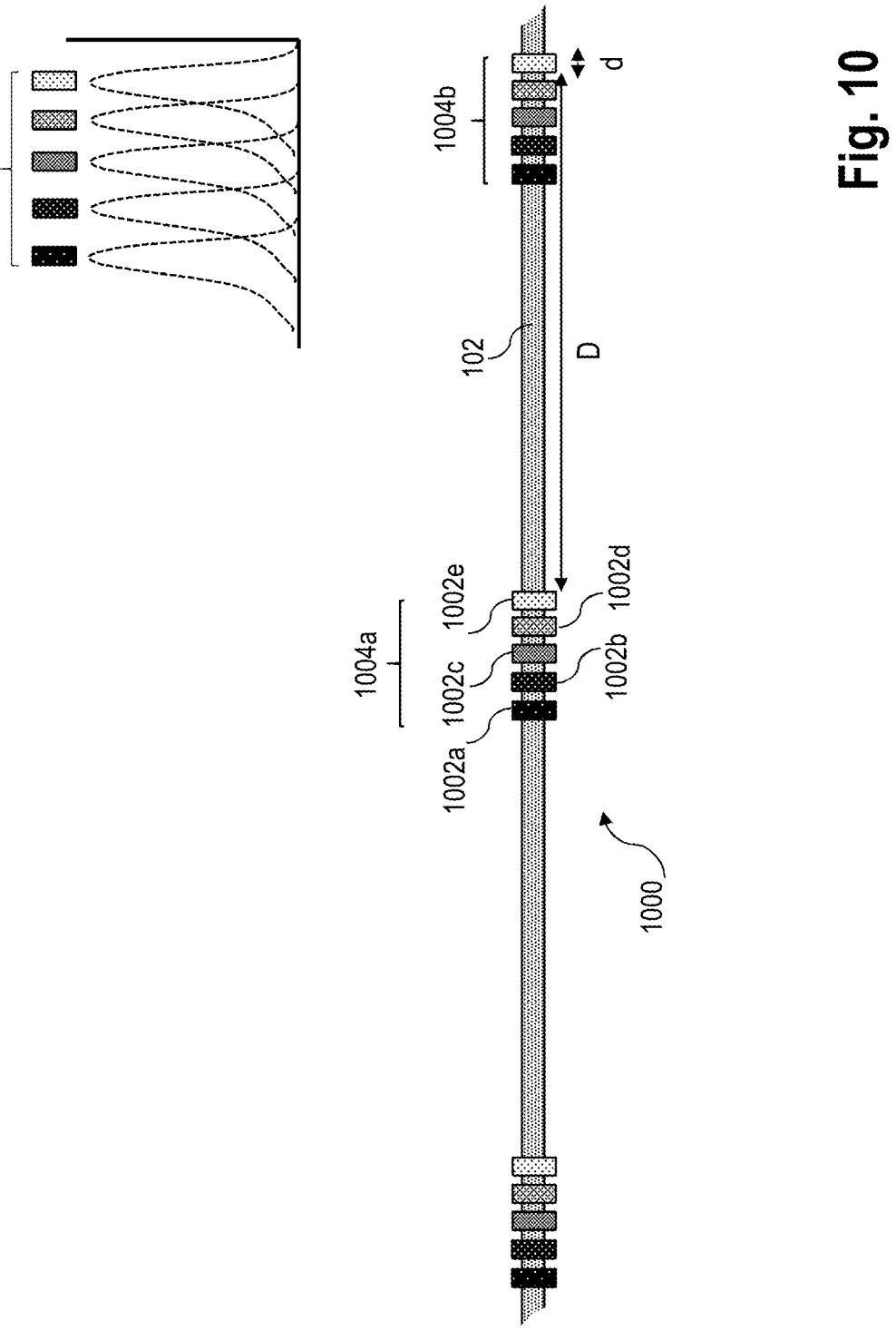
FIG. 10 shows a detailed view of second embodiment of the capture construct with several pluralities of capture regions.

FIGS. 8 to 10 show options for reading out the capture construct 100, in particular the capture regions 108a to 108f, 500, 600, 700.

FIG. 8 shows a column of illumination and detection points spread functions (PSFs) 800a and a column of corresponding effective PSFs 800b. Unless noted otherwise PSF refers to the main maximum of the PSF in this document. Most microscopes illuminate and detect the sample through the same objective. In this case both the illumination PSF 802a and the detection PSF 804 are elliptical. In the case of light sheet fluorescence microscopy for example the illumination PSF 802b may be sheet-like and the detection PSF 804 may be elliptical, which still leads to an elliptical PSF provided that the detection PSF 804 is fully illuminated.

In the case of multi-view imaging with multiple detection PSFs placed at an angle 804a-804f, which may or may not be combined with light sheet illumination, effective PSFs 806c, 806d can be achieved, which are substantially improved over the elliptical PSFs 806a, 806b. Generally, an isotropic PSF improves the ability to resolve distinct capture regions 108a to 108f, 500, 600, 700 on a nanoarray and renders this also largely invariant to the orientation of the nanoarray. In other words, if an imaging system with an elliptical effective PSF 806a is used, then the resolving power in the axial direction (a) is lower than the in lateral direction (l). In the case of PSF 806d and PSF 806c the resolving power would be comparable in all room directions, which is not required for reading out nanoarrays, in particular capture regions 108a to 108f, 500, 600, 700, but may be preferable.

FIG. 9 shows a detailed view of the capture construct 100. The capture regions 108a to 108f are at distance from each other of 500 nm, as described above. The capture regions 108a to 108f may be read out by a readout device having the PSF 806a or the PSF 806d, as described for FIG. 8. The capture regions 108a to 108f are distanced from each other such that the readout device can resolve the capture regions 108a to 108f individually. Thus, all the affinity reporter reagents of the capture construct 100 may comprise the same dye.

FIG. 10 shows a detailed view of a capture construct 1000 with several pluralities of capture regions. The capture construct comprises a first plurality 1002a, a second plurality 1002b, a third plurality 1002c, a fourth plurality 1002d and a fifth plurality 1002e of capture regions. The reference signs 1002a to 1002e refer to one of the capture regions of the respective plurality. The capture regions 1002a to 1002e are grouped with each group 1004a, 1004b comprising one of each of the capture regions 1002a to 1002e. The groups 1004a, 1004b are distance (D) from each other by 500 nm along the backbone 102. Each capture region 1002a to 1002e is approximately 25 nm wide (d) along the backbone 102.

The capture regions 1002a to 1002e may be read out by the readout device having the PSF 806a or the PSF 806d, as described for FIGS. 8 and 9. However, in order to differentiate between the capture regions 1002a to 1002e of each group 1004a, 1004b with the readout device, the affinity reporter reagents of the capture construct 1000 comprise different dyes. Specifically, the affinity reporter reagents of the plurality of capture regions 1002a to 1002e comprises a dye with characteristics unique to each of the plurality of capture regions 1002a to 1002e. This enables reading out individual capture regions 1002a to 1002e of a single group 1004a, 1004b.

This results in an increased density of capture regions 1002a to 1002e of capture construct 1000 and an accompanying vastly increased number of capture regions 1002a to 1002e compared to the capture construct 100 in FIG. 1.

Figure 11:
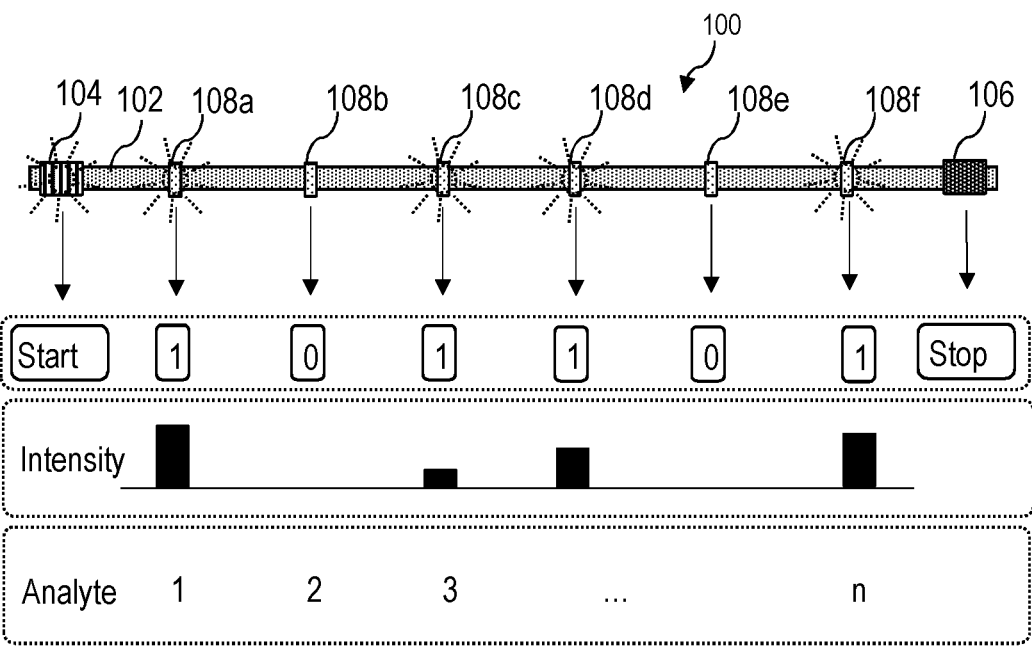
FIG. 11 schematically illustrates read out data from the capture constructs according to some embodiments.
Figure 11:
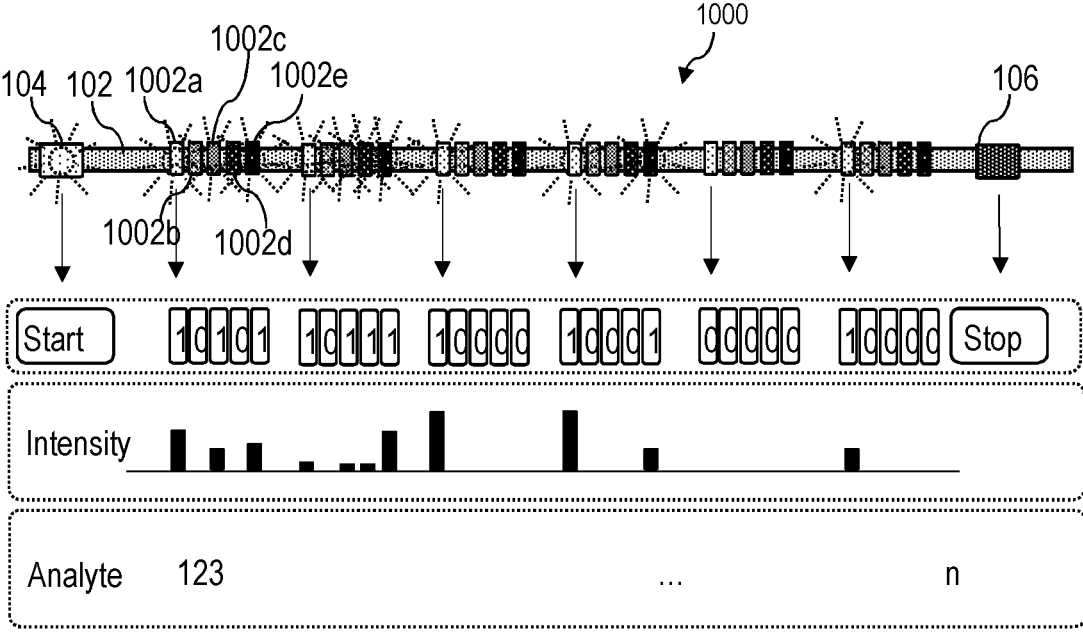

FIG. 11 schematically illustrates read out data from the capture construct 100 and 1000. The optical signal determined from reading out the capture regions 108a to 108f, 1002a to 1002e may be categorised in a binary code of "0'"s and "1"s, wherein a fluorescent signal from the analyte being present results in a "1" and no fluorescent signal when the analyte is absent results in a "0". A given sequence 0101010 for example can be interpreted or decoded for a given capture construct with known affinity reagents at each location of the capture regions and the directionality of the capture construct based on the orientation indicators 104, 106. This means, that the identities of analytes can be computed from a given sequence, or simply looked up in a memory file or database. In addition to providing a binary answer to the question whether a certain analyte was detected or not, the method provides intensity information, which can be used for relative quantification (i.e. analyte 1 has a 5× higher signal than analyte 2) or absolute quantification (i.e. the intensity read for analyte 1 corresponds to 10 dye molecules, which correspond to 5 analyte molecules for example).

15

Figure 12:
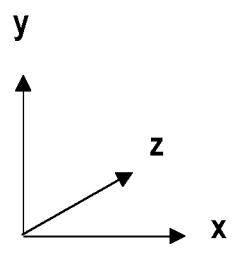
FIG. 12 shows capture constructs with different geometries according to some embodiments.
Figure 12:
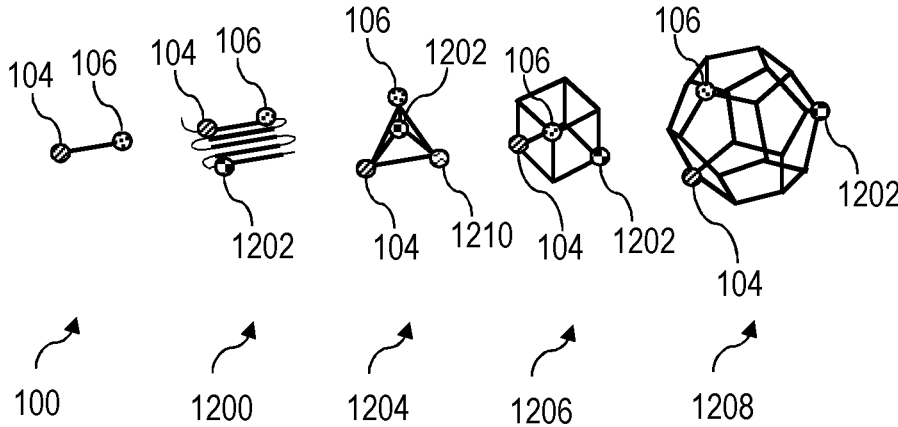

FIG. 12 shows capture constructs with different geometries. A sheet-like capture construct 1200, which may be a large linear DNA molecule or an assembly of multiple DNA molecules. Sheet-like nanoarrays may increase the number of available capture regions substantially. In order to be able to determine the orientation of the capture construct 1200, a third orientation indicator 1202 is provided.

Further geometries are possible, for example, a tetrahedral capture construct 1204, a cubic capture construct 1206, or a polyhedral capture construct 1208. These may comprise a fourth orientation indicator 1210 in order to determine their orientation.

Figure 13:
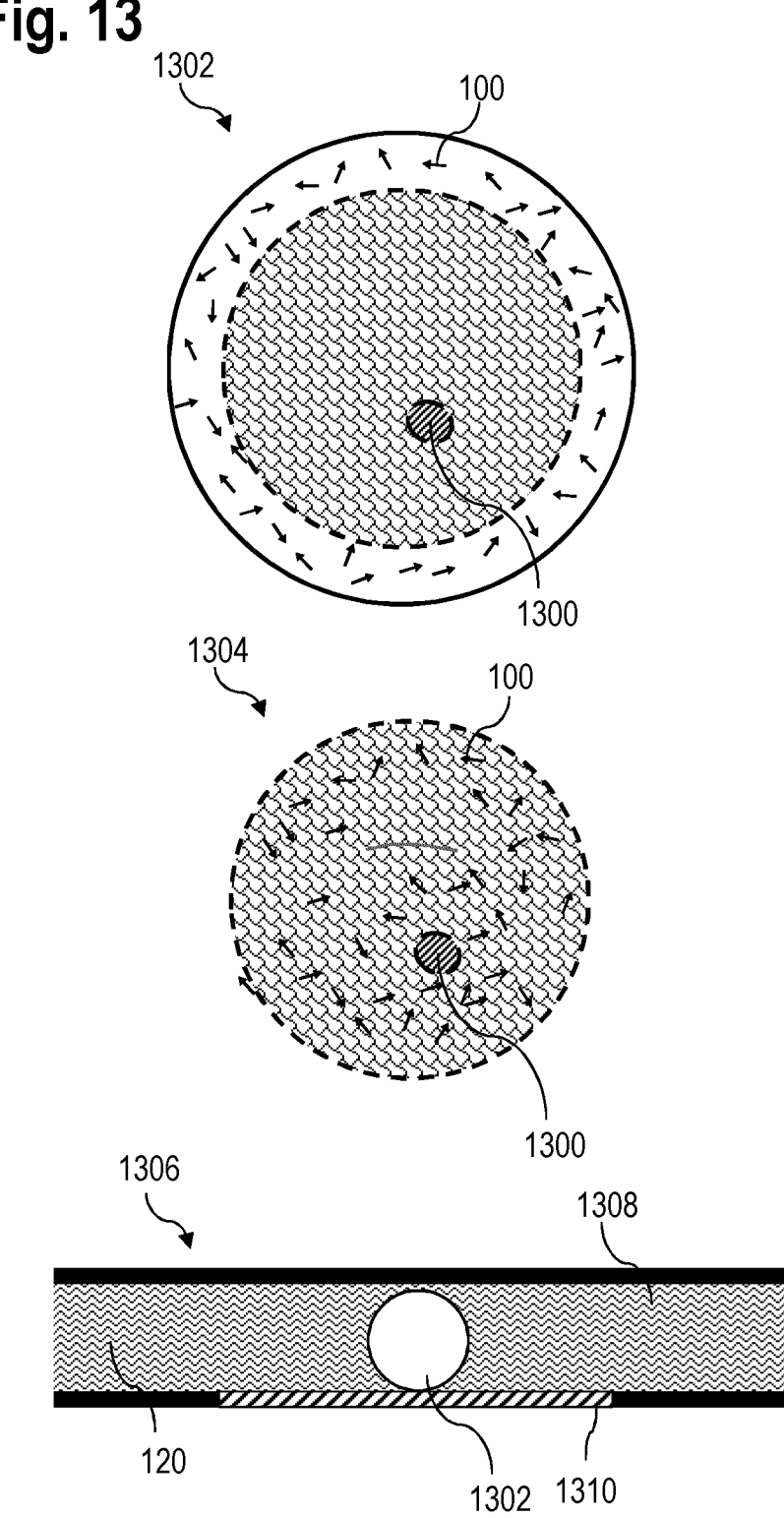
FIG. 13 shows the capture construct according to FIG. 1 with a biological sample embedded in a hydrogel bead, according to some embodiments.

FIG. 13 shows the capture construct 100 with a biological sample 1300 embedded in a hydrogel bead 1302. The hydrogel bead 1302 is a multi-phasic hydrogel bead with a phase for cultivation of the biological sample 1300, such as a single cell or multiple cells in 3D cell culture, and at least one further layer which may be internal to or surrounding the cultivation phase/layer. The at least one further layer may be of the same or a different material. Alternatively, the biological sample 1300 and the capture construct 100 may be embedded in a single-phase hydrogel bead 1304

The biological sample 1300 encapsulated in the hydrogel bead 1302 may be cultivated and secrete proteins. For example, immune cells may be isolated following a liquid biopsy from a tumour patient or a patient that has an infectious disease, in order to study the immunophenotype, and/or immunorepertoire, and/or immunocompetence of the patient and to determine the best course of treatment. Secreted molecules are of great interest in this regard, for example as cytokines, and are indicative of the activation status of certain immune cells. Embodiments of the present invention leverage nanoarrays, which may be preferentially based on DNA-origami, carrying capture regions that capture analytes of interest.

The readout device may comprise a flow cell 1306 through which the hydrogel beads 1302, 1304 may flow in a liquid 1308. The flow cell 1306 comprises an optical window 1310 through which the hydrogel beads 1302, 1304, in particular the capture construct 100, 1000 may be imaged by an optical imaging device, such as a microscope.

Figure 14:
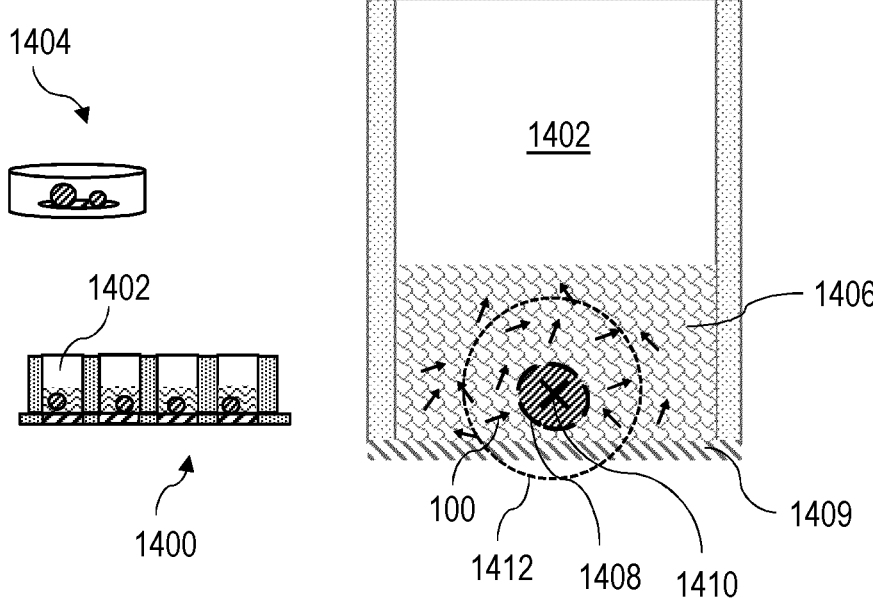
FIG. 14 shows sample containers with biological samples according to some embodiments.

FIG. 14 shows sample containers with biological samples such as single cells embedded in a hydrogel gel. For example, a microplate 1400 with sample wells 1402 and a petri dish 1404. The capture construct 100, 1000 may be in suspension in a liquid or embedded in a hydrogel 1406 inside the sample well 1402 together with a biological sample 1408 such as a single cell or a multicellular structure under cultivation. The readout device may image the contents of the well 1402 through an optical window 1409 and determine the centre of mass 1410 of the biological sample 1408 and the capture constructs 100 that are situated within a predetermined radius 1412 of the centre of mass 1410 of the biological sample 1408.

Thus, in order to capture and detect secreted target analytes of the biological sample 1300, 1408 by means of the capture construct 100, 1000, the biological sample 1300, 1408 is incubated in the presence of the capture construct 100, 1000, or a plurality of the capture constructs 100, 1000, comprising capture regions with affinity capture reagents that bind the target analytes. This enables the analytes secreted by the biological sample 1300, 1408 to be captured by the capture construct 100, 1000, in particular the corresponding affinity capture reagents. Subsequently a readout of at least the capture construct 100, 1000, in particular the capture regions and the orientation indicators, is acquired. This readout may be acquired by means of an optical device, such as a microscope or an imaging flow cytometer. Based on the readout, the capture regions are then assessed to determine whether or not the respective target analytes are captured by the capture regions of the capture construct.

As used herein the term "and/or" includes any and all combinations of one or more of the associated listed items and may be abbreviated as "/".

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus.

While subject matter of the present disclosure has been illustrated and described in detail in the drawings and foregoing description, such illustration and description are to be considered illustrative or exemplary and not restrictive. Any statement made herein characterizing the invention is also to be considered illustrative or exemplary and not restrictive as the invention is defined by the claims. It will be understood that changes and modifications may be made, by those of ordinary skill in the art, within the scope of the following claims, which may include any combination of features from different embodiments described above.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

LIST OF REFERENCE SIGNS

100, 1000 Capture construct
102 Nanostructure backbone
104, 106, 1202, 1210 Orientation indicator
108a, 108b, 108c,
108d, 108e, 108f,
500, 600, 700, 1002a,
1002b, 1002c, 1002d,
1002e Capture region
200a, 200b, 200c,
200d, 200e, 200f Affinity reagent
202, 204, 208 Oligonucleotide tag
206a, 206b, 508, 708,
710 Dye
300a, 300b, 300c,
300d, 300e, 300f,
506, 606 Affinity reporter reagent
400, 502, 602, 702,
704 Affinity capture reagent
402, 504, 604, 706 Analyte
404 Readout 800*a* Column of illumination and detection points spread functions
800*b* Column of effective point spread functions
802*a*, 802*b* Illumination point spread function
804, 804*a*, 804*b*,
804*c*, 804*d*, 804*e*,
804*f* Detection point spread function
806*a*, 806*b* Elliptical effective point spread function
806*c*, 806*d* Isotropic point spread function
1004*a*, 1004*b* Group of capture regions
1300, 1408 Biological sample
1302, 1304 Hydrogel bead
1306 Flow cell
1308 Liquid
1310, 1409 Optical window
1400 Microplate
1402 Sample wells
1404 Petri dish
1406 Hydrogel or 3D cell culture matrix
1410 Centre of mass

The invention claimed is:

1. A capture construct for capturing a plurality of analytes of a biological sample, the capture construct comprising:
a nanostructure backbone,
at least a first orientation indicator and a second orientation indicator, wherein the first orientation indicator and the second orientation indicator are spaced apart from each other, or arranged on opposite ends of the nanostructure backbone,
at least a first plurality of capture regions on the nanostructure backbone, each capture region comprising at least one affinity capture reagent, configured to capture one of the plurality of analytes, and
at least one first affinity reporter reagent comprising a first reporter tag and configured to attach to an analyte of the plurality of analytes, wherein the first reporter tag is optically readable, to determine whether or not the respective analyte is captured by the at least one affinity capture reagent.

2. The capture construct according to claim 1, wherein the nanostructure backbone comprises nucleic acids.

3. The capture construct according to claim 1, wherein the at least one affinity capture reagent comprises an antibody, an antibody fragment, an oligonucleotide, an aptamer, a peptide, a drug, and/or a toxin, or a combination thereof.

4. The capture construct according to claim 1, wherein the at least one first affinity reporter reagent includes a first plurality of affinity reporter reagents, each affinity reporter reagent comprising the first reporter tag.

5. The capture construct according to claim 4, wherein each affinity reporter reagent comprises an antibody, an antibody fragment, an oligonucleotide, an aptamer, a peptide, a drug, and/or a toxin, or a combination thereof.

6. The capture construct according to claim 4, wherein the first reporter tag comprises an oligonucleotide and is readable by sequencing.

7. The capture construct according to claim 1, wherein the at least one affinity capture reagent is bound to the nanostructure backbone, or
wherein the at least one affinity capture reagent of a particular capture region of the first plurality of capture regions comprises an oligonucleotide, and the particular capture region comprises a complementary oligonucleotide to bind to the oligonucleotide of the at least one affinity capture reagent.

8. The capture construct according to claim 1, wherein the nanostructure backbone comprises at least a second plurality of capture regions, each capture region of the second plurality of capture regions comprising at least one affinity capture reagent configured to capture one of the plurality of analytes.

9. The capture construct according to claim 8, further comprising a second plurality of affinity reporter reagents , each affinity reporter reagent of the second plurality of affinity reporter reagents comprising a second reporter tag and configured to attach to a respective analyte of the plurality of analytes, wherein the second reporter tag is readable, to determine whether or not the respective analyte is captured by the respective affinity capture reagent.

10. The capture construct according to claim 1, wherein the nanostructure backbone extends linearly in one dimension.

11. The capture construct according to claim 1, wherein the nanostructure backbone extends in two dimensions or three dimensions, and the nanostructure backbone comprises at least a third orientation indicator.

12. The capture construct according to claim 1, wherein a largest spatial extent of the nanostructure backbone is in a range from 1 nm to 10000 nm.

13. The capture construct according to claim 1, wherein the capture regions of the first plurality of capture regions are spaced apart from each other in a range from 1 nm to 2000 nm.

14. The capture construct according to claim 8, wherein the capture regions of the first plurality of capture regions are spaced apart from the capture regions of the second plurality of capture regions in a range from 0.1 nm to 500 nm.

15. The capture construct according to claim 4, wherein the first reporter tags comprise fluorophores with differing excitation wavelengths, differing fluorescence emission wavelengths, and/or differing fluorescence lifetime characteristics.

16. The capture construct according to claim 1, wherein the affinity capture reagent of at least one of the first plurality of capture regions is configured to bind a respective analyte of the plurality of analytes at a single binding site of the respective analyte.

17. The capture construct according to claim 1, wherein at least one capture region of the first plurality of capture regions comprises a first set of affinity capture reagents and a second set of affinity capture reagents, and wherein the first set of affinity capture reagents is configured to bind one analyte of the plurality of analytes at a first binding site of the one analyte and the second set of affinity capture reagents is configured to bind the one analyte of the plurality of analytes at a second binding site of the one analyte.

18. The capture construct according to claim 17, wherein the first set of affinity capture reagents comprises first capture reagent dyes, and the second set of affinity capture reagents comprises second capture reagent dyes, wherein the first capture reagent dyes and the second capture reagent dyes are fluorophores.

19. The capture construct according to claim 18, wherein the first capture reagent dyes and the second capture reagent dyes are configured to be brought into a proximity when the one analyte is captured by one of the affinity capture reagents of the first set of affinity capture reagents and by one of the affinity capture reagents of the second set of affinity capture reagents, and wherein the proximity enables an energy transfer between the first capture reagent dyes and the second capture reagent dyes.

20. The capture construct according to claim 1, wherein the capture construct and the biological sample are embedded in or attached to a polymeric compound.

21. A method for detecting a plurality of analytes of a biological sample, the method comprising the following steps:

incubation of the biological sample in a presence of at least one capture construct according to claim 1, acquiring a read-out of at least the one capture construct, and determining whether or not a respective analyte is captured by the respective affinity capture reagent.

\* \* \* \* \*